(12) United States Patent
Genov et al.

(10) Patent No.: US 11,172,857 B2
(45) Date of Patent: Nov. 16, 2021

(54) SYSTEM, SYSTEM ARCHITECTURE, AND METHOD FOR NEURAL CROSS-FREQUENCY COUPLING ANALYSIS

(71) Applicant: THE GOVERNING COUNCIL OF THE UNIVERSITY OF TORONTO, Toronto (CA)

(72) Inventors: Roman Genov, Toronto (CA); Gerard O'Leary, Toronto (CA)

(73) Assignee: THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 596 days.

(21) Appl. No.: 16/032,190

(22) Filed: Jul. 11, 2018

(65) Prior Publication Data

US 2020/0015692 A1 Jan. 16, 2020

(51) Int. Cl.
  *A61B 5/24* (2021.01)
  *A61B 5/316* (2021.01)
  (Continued)

(52) U.S. Cl.
  CPC ............... *A61B 5/24* (2021.01); *A61B 5/316* (2021.01); *A61B 5/374* (2021.01); *A61B 5/4064* (2013.01); *A61B 5/7225* (2013.01)

(58) Field of Classification Search
  CPC ........... A61B 5/24; A61B 5/316; A61B 5/374; A61B 5/4064; A61B 5/7225; A61B 5/4082; A61B 5/6868
  (Continued)

(56) References Cited

U.S. PATENT DOCUMENTS 4,705,049 A * 11/1987 John ..................... A61B 5/377
                                                       600/544
6,597,954 B1    7/2003 Pless et al.
                  (Continued)

FOREIGN PATENT DOCUMENTS

CN        102157989        8/2011
WO     2015092747 A2       6/2015
                  (Continued)

OTHER PUBLICATIONS

International Search Report corresponding to PCT/CA2016/050655; Canadian Intellectual Property Office; dated Sep. 7, 2016.
(Continued)

*Primary Examiner* — Navin Natnithithadha
(74) *Attorney, Agent, or Firm* — Bhole IP Law; Anil Bhole; Marc Lampert

(57) ABSTRACT

There is provided a system, system architecture, and method for neural cross-frequency coupling analysis. In an embodiment, the method includes: receiving neural signals; extracting a phase frequency signal and an amplitude frequency envelope signal from each of the neural signals; determining a first measure of cross-frequency coupling comprising a mean vector length modulation index (MVL-MI), determining the MVL-MI comprises determining a magnitude of an averaged complex-valued time series from a plurality of samples of the neural signals to extract a phase-amplitude coupling measure, each sample associated with a respective one of the amplitude frequency envelope signals and the phase frequency signals; and outputting at least one measure of the cross-frequency coupling.

19 Claims, 14 Drawing Sheets

(51) Int. Cl.
  *A61B 5/374* (2021.01)
  *A61B 5/00* (2006.01)
(58) Field of Classification Search
  USPC .......................................................... 600/544
  See application file for complete search history.

(56) References Cited

U.S. PATENT DOCUMENTS

| | | | |
|---|---|---|---|
| 7,212,110 | B1 | 5/2007 | Martin et al. |
| 8,180,452 | B2 | 5/2012 | Shaquer |
| 9,295,838 | B2* | 3/2016 | Starr .................. A61N 1/36067 |
| 9,604,056 | B2* | 3/2017 | Starr .................. A61N 1/36067 |
| 2004/0068199 | A1 | 4/2004 | Echauz et al. |
| 2007/0067003 | A1 | 3/2007 | Sanchez et al. |
| 2007/0150024 | A1 | 6/2007 | Leyde et al. |
| 2007/0213786 | A1 | 9/2007 | Sackellares et al. |
| 2008/0007645 | A1 | 1/2008 | McCutchen |
| 2010/0197524 | A1 | 8/2010 | Janata et al. |
| 2011/0074995 | A1 | 3/2011 | Rafferty et al. |
| 2011/0130797 | A1 | 6/2011 | Talathi et al. |
| 2011/0266416 | A1 | 11/2011 | Kurimoto et al. |
| 2012/0078071 | A1 | 3/2012 | Bohm et al. |
| 2013/0172774 | A1 | 7/2013 | Crowder et al. |
| 2014/0163627 | A1* | 6/2014 | Starr .................. A61N 1/0531 607/3 |
| 2014/0252201 | A1 | 9/2014 | Li et al. |
| 2014/0267855 | A1 | 9/2014 | Fan |
| 2014/0316217 | A1* | 10/2014 | Purdon .............. A61B 5/14542 600/301 |
| 2016/0361546 | A1 | 12/2016 | Salam et al. |
| 2018/0115725 | A1 | 4/2018 | Zhang et al. |
| 2018/0214054 | A1 | 8/2018 | Soltani et al. |

FOREIGN PATENT DOCUMENTS

| | | |
|---|---|---|
| WO | 2017059540 A1 | 4/2017 |
| WO | 2018014127 A1 | 1/2018 |

OTHER PUBLICATIONS

Written Opinion of the International Searching Authority corresponding to PCT/CA2016/050655; Canadian Intellectual Property Office; dated Sep. 7, 2016.
"The 128-Channel Fully Differential Digital Integrated Neural Recording and Stimulation Interface" Shahrokhi et al [online], May 24, 2010 (May 24, 2010), [Retrieved on Oct. 12, 2017 (Oct. 12, 2017). Retrieved from: http://ieeexplore.ieee.org/document/5471738/authors?part=1.
"Design of an Optimal & Closed-Loop Neurostimulation System for treatment of Epilepsy" Gao, Richard, [online], Nov. 23, 2015 (Nov. 23, 2015], Retrieved on Oct. 12, 2017 (Oct. 12, 2017). Retrieved from: http:www,undergraduatelibrary.org/2014/medical-sciences/design-optimal-closed-loop-neuromodulation-system-treatment-epilepsy.
"Micropower CMOS Integrated Low-Noise Amplification, Filtering, and Digitization of Multimodal Neuroptentials" Mollazadeh et al. [online], Jan. 1, 2010 (Jan. 1, 2010). Retrieved Oct. 12, 2017 (Oct. 12, 2017). Retrieved from: https://www.ncbi.nlm.nih.gov/pmc/articles/PMC2747318/.
Bagheri, A., et al. (2013) Massively-Parallel Neuromonitoring and Neurostimulation Rodent Headset With Nanotextured Flexible Microelectrodes. IEEE Transactions on Biomedical Circuits and Systems, 7:601-609.
Medeiros, D.D., Moraes M.F. (2014) Focus on Desynchronization Rather Than Excitability: A New Strategy for Intraencephalic Electrical Stimulation. Epilepsy Behav, 38C:32-36.
Jiruska, P., et al. (2010) Effects of Direct Brain Stimulation Depend on Seizure Dynamics. Epilepsia 51:93-97.
Lockman, J., Fisher, R.S. (2009) Therapeutic Brain Stimulation for Epilepsy. Neurologic Clinics 27:1031-1040.
Sun, F.T., Morrell, M.J. (2014) The RNS System: Responsive Cortical Stimulation for the Treatment of Refractory Partial Epilepsy. Expert Review of Medical Devices, 11:563-572.
Krook-Magnuson, E., et al. (2013) On-Demand Optogenetic Control of Spontaneous Seizures in Temporal Lobe Epilepsy. Nature Communications, 4:1376.
Weiss, S.R., et al., (1995) Quenching: Inhibition of Development and Expression of Amygdala Kindled Seizures With Low Frequency Stimulation. Neuroreport, 6:2171-2176.
Tergau, F., et al. (1999) Low-Frequency Repetitive Transcranial Magnetic Stimulation Improves Intractable Epilepsy. Lancet, 353:2209.
Koubeissi, M.Z. et al., (2013) Low-Frequency Electrical Stimulation of a Tiber Tract in Temporal Lobe Epilepsy. Annals of Neurology, 74:223-231.
Colpan, M.E., et al., (2007) Proportional Feedback Stimulation for Seizure Control in Rats. Epilepsia, 48:1594-1603.
Good, L.B. et al., (2009) Control of Synchronization of Brain Dynamics Leads to Control of Epileptic Seizures in Rodents. International Journal of Neural Systems, 19:173-196.
Rashid, S. et al. (2012)Low Frequency Stimulation of Ventral Hippocampal Commissures Reduces Seizures in a Rat Model of Chronic Temporal Lobe Epilepsy. Epilepsia, 53:147-156.
Osorio, I., Frei M.G. (2009) Seizure Abatement With Single DC Pulses: Is Phase Resetting at Play? International Journal of Neural Systems, 19:149-156.
International Search Report corresponding to PCT/CA2016/051169; Canadian Intellectual Property Office; dated Jan. 13, 2017.
Written Opinion of the International Searching Authority corresponding to PCT/CA2016/051169; Canadian Intellectual Property Office; dated Jan. 13, 2017.
International Search Report corresponding to PCT/2017/050867; Canadian Intellectual Property Office; dated Oct. 18, 2017.
Written Opinion of the International Searching Authority corresponding to PCT/CA2017/050867; Canadian Intellectual Property Office; dated Oct. 18, 2018.
Office Action for U.S. Appl. No. 15/177,615; USPTO; dated Oct. 6, 2017.
International Search Report corresponding to PCT/2018/050496; Canadian Intellectual Property Office; dated Jul. 27, 2018.
Written Opinion of the International Searching Authority corresponding to PCT/CA2018/050496; Canadian Intellectual Property Office; dated Jul. 27, 2018.
Bamji, C.S., O'Connor, P., Elkhatib, T., Mehta, S., Thompson, B., Prather, L.A., Snow, D., Akkaya, O.C., Daniel, A., Payne, A.D., Perry, T., Fenton, M., Chan, V.H.: A 0.13 µm CMOS System-on-Chip for a 512×424 Time-of-Flight Image Sensor With Multi-Frequency Photo-Demodulation up to 130 MHz and 2 GS/s ADC. IEEE-JSSC 50(1) 303-319.
Newcombe, R.A., Fox, D., Seitz, S., 2015: DynamicFusion: Reconstruction and tracking of non-rigid scenes in real-time. In: IEEE CVPR 2015.
Heide, F., Hullin, M.B., Gregson, J., Heidrich, W.: Low-budget Transient Imaging Using Photonic Mixer Devices. In: ACM SIGGRAPH, New York, NY, USA, ACM Request Per-missions (2013).
Shrestha, S., Heide, F., Heidrich, W., Wetzstein, G.: Computational imaging with multi-camera time-of-flight systems. In: Proc. ACM SIGGRAPH Asia, ACM (Jul. 2016) 33-11.
Lichtsteiner, P., Posch, C., Delbruck, T.: A 128×128 120 dB 15 µs Latency Asynchronous Temporal Contrast Vision Sensor. IEEE-JSSC 43(2) 566-576.
Kim, H., Leutenegger, S., Davison, A.J.: Real-Time 3D Reconstruction and 6-DoF Tracking with an Event Camera. In: Proc. ECCV, Cham, Springer, Cham (Oct. 2016) 349-364.
Zhang, J., Etienne-Cummings, R., Chin, S., Xiong, T., Tran, T.: Compact all-CMOS spatiotemporal compressive sensing video camera with pixel-wise coded exposure. Opt Express 24(8) (2016) 9013-9024.
Luo, Y., Ho, D., Mirabbasi, S.: Exposure-Programmable CMOS Pixel With Selective Charge Storage and Code Memory for Computational Imaging. IEEE Trans. Circuits Syst. 11-12.
Sonoda, T., Nagahara, H., Endo, K., Sugiyama, Y., Taniguchi, R.i.: High-speed imaging using CMOS image sensor with quasi pixel-wise exposure. In: IEEE ICCP, IEEE.

(56) References Cited

OTHER PUBLICATIONS

Baraniuk, R.G., Goldstein, T., Sankaranarayanan, A.C., Studer, C., Veeraraghavan, A., Wakin, M.B.: Compressive Video Sensing: Algorithms, architectures, and applications. IEEE Signal Proc. Mag. 34(1) 52-66.

Jang, J., Yoo, Y., Kim, J., Paik, J.: Sensor-Based Auto-Focusing System Using Multi-Scale Feature Extraction and Phase Correlation Matching. In: Sensors, Multidisciplinary Digital Publishing Institute (2015) 5747-5762.

Yasuma, F., Mitsunaga, T., Iso, D., Nayar, S.K.: Generalized Assorted Pixel Camera: Post-capture Control of Resolution, Dynamic Range, and Spectrum. IEEE-TIP 19(9) 2241-2253.

Heintzmann, R., Hanley, Q.S., Arndt-Jovin, D., Jovin, T.M.: A dual path programmable array microscope (PAM): simultaneous acquisition of conjugate and non-conjugate images. J. Microscopy 204 (2001) 119-135.

O'Toole, M., Achar, S., Narasimhan, S.G., Kutulakos, K.N.: Homogeneous codes for energy-efficient illumination and imaging. In: Proc. ACM SIGGRAPH Asia, ACM Request Per-missions (2015).

O'Toole, M., Mather, J., Kutulakos, K.N.: 3D Shape and Indirect Appearance by Structured Light Transport. IEEE T-PAMI 38(7) (2016) 1298-1312.

Hernandez, C., Vogiatzis, G., Brostow, G.J., Stenger, B., Cipolla, R.: Non-rigid Photometric Stereo with Colored Lights. In: Proc. IEEE ICCP. (2007).

Fyffe, G., Yu, X., Debevec, P.: Single-shot photometric stereo by spectral multiplexing. In: Proc. IEEE ICCP. (2011).

Van der Jeught, S., Dirckx, J.J.J.: Real-time structured light profilometry: a review. Optics and Lasers in Engineering 87 (2016) 18-31.

Sagawa, R., Furukawa, R., Kawasaki, H.: Dense 3D Reconstruction from High Frame-Rate Video Using a Static Grid Pattern. IEEE T-PAMI 36(9) 1733-1747.

Gharbi, M., Chaurasia, G., Paris, S., Durand, F.: Deep joint demosaicking and denoising. Proc. ACM SIGGRAPH Asia 35(6) (Nov. 2016) 191-12.

Heide, F., Steinberger, M., Tsai, Y.T., Rouf, M., Pajak, D., Reddy, D., Gallo, O., Liu, J., Heidrich, W., Egiazarian, K., Kautz, J., Pulli, K.: FlexISP: a flexible camera image processing framework. In: Proc. ACM SIGGRAPH Asia, ACM Request Permissions (2014).

Liu, Z., Shan, Y., Zhang, Z.: Expressive expression mapping with ratio images. In: Proc. ACM SIGGRAPH, New York, New York, USA, ACM (2001) 271-276.

Davis, J., Yang, R., Wang, L.: BRDF invariant stereo using light transport constancy. In: Proc. IEEE ICCV. (2005) 436-443 vol. 1.

Pilet, J., Strecha, C., Fua, P.: Making Background Subtraction Robust to Sudden Illumination Changes. In: Proc. ECCV, Berlin, Heidelberg, Springer, Berlin, Heidelberg (2008) 567-580.

Lange, R., Seitz, P.: Solid-state time-of-flight range camera. IEEE J. Quantum Electron. 37(3) (2001) 390-397.

Wan, G., Li, X., Agranov, G., Levoy, M., Horowitz, M.: CMOS Image Sensors With Multi-Bucket Pixels for Computational Photography. IEEE-JSSC 47(4) (Apr. 2012) 1031-1042.

Wan, G., Horowitz, M., Levoy, M.: Applications of Multi-Bucket Sensors to Computational Photography. Technical Report 2012-2, Stanford Computer Graphics Lab.

Wetzstein, G., Ihrke, I., Heidrich, W.: On Plenoptic Multiplexing and Reconstruction. Int. J. Computer Vision 101(2) (Jan. 2013) 384-400.

Ratner, N., Schechner, Y.Y., Goldberg, F.: Optimal multiplexed sensing: bounds, conditions and a graph theory link. Opt Express 15(25) (Dec. 2007) 17072-17092.

Brown, C.M.: Multiplex Imaging and Random Arrays. PhD thesis, PhD Dissertation, University of Chicago (1972).

Schechner, Y.Y., Nayar, S.K., Belhumeur, P.N.: Multiplexing for optimal lighting. IEEE T-PAMI 29(8) (Jun. 2007) 1339-1354.

Ratner, N., Schechner, Y.Y.: Illumination Multiplexing within Fundamental Limits. In: 2007 IEEE Conference on Computer Vision and Pattern Recognition, IEEE (2007) 1-8.

Nonoyama, M., Sakaue, F., Sato, J.: Multiplex Image Projection Using Multi-band Projectors. In: 2013 IEEE International Conference on Computer Vision Workshops (ICCVW), IEEE (2013) 868-873.

Mitra, K., Cossairt, O.S., Veeraraghavan, A.: A Framework for Analysis of Computational Imaging Systems: Role of Signal Prior, Sensor Noise and Multiplexing. IEEE T-PAMI 36(10) (2014) 1909-1921.

Raskar, R., Agrawal, A., Tumblin, J.: Coded exposure photography: motion deblurring using fluttered shutter. In: Proc. ACM SiGGRAPH. (2006).

Wu, L., Ganesh, A., Shi, B., Matsushita, Y., Wang, Y., Ma, Y.: Robust Photometric Stereo 707 via Low-Rank Matrix Completion and Recovery. In: Proc. ACCV. (2010).

Gupta, M., Nayar, S.: Micro Phase Shifting. In: Proc. IEEE CVPR. (2012) 813-820.

Queau, Y., Mecca, R., Durou, J.D., Descombes, X.: Photometric stereo with only two images: A theoretical study and numerical resolution. Image and Vision Computing 57 (Jan. 2017) 175-191.

\* cited by examiner

SYSTEM, SYSTEM ARCHITECTURE, AND METHOD FOR NEURAL CROSS-FREQUENCY COUPLING ANALYSIS

TECHNICAL FIELD

The following relates, generally, to signal processing; and more particularly, to a system, system architecture, and method for neural cross-frequency coupling analysis.

BACKGROUND

Cross-frequency coupling (CFC), it is suggested, is a key mechanism in neuronal computation, communication, and learning in the brain. Abnormal CFC has been implicated in pathological brain states such as epilepsy and Parkinson's disease. A reduction in excessive coupling has been shown in effective neuromodulation treatments, suggesting that CFC may be a useful feedback measure in closed-loop neural stimulation devices. However, processing latency limits the responsiveness of conventional systems.

SUMMARY

In an aspect, there is provided a system for neural cross-frequency coupling analysis, the system connectable to one or more neural signal receivers to receive neural signals, the system comprising one or more processors and one or more memory units, the one or more processors in communication with the one or more memory units and configured to execute: a modulation signal extractor module to extract a phase frequency signal and an amplitude frequency envelope signal from each of the neural signals; a mean vector length (MVL) module to determine a first measure of cross-frequency coupling comprising a mean vector length modulation index (MVL-MI), determining the MVL-MI comprises determining a magnitude of an averaged complex-valued time series from a plurality of samples of the neural signals to extract a phase-amplitude coupling measure, each sample associated with a respective one of the amplitude frequency envelope signals and the phase frequency signals; and an output module to output at least one measure of the cross-frequency coupling.

In a particular case, the one or more processors are further configured to execute a phase locking value (PLV) module to determine a second measure of cross-frequency coupling comprising a cross-frequency phase locking value (CF-PLV) between a phase of the phase frequency signal and a phase of the amplitude frequency envelope signal.

In another case, the one or more processors are further configured to execute a heights ratio (HR) module to determine a third measure of a heights ratio between a maximum amplitude height and a minimum amplitude height of the amplitude frequency envelope.

In yet another case, the modulation signal extractor module extracts the amplitude frequency envelope signal by passing the neural signal through a Hilbert filter, creating a complex vector comprising real and imaginary components, and determining the magnitude of the complex vector.

In yet another case, determining the CF-PLV comprises: determining an angular difference as the phase of the phase frequency signal subtracted by the phase of the amplitude frequency envelope signal; determining an instantaneous complex vector from the angular difference averaged over the plurality of samples; and determining a magnitude of the instantaneous vector as a measure of phase locking value.

In yet another case, when the magnitude of the instantaneous vector is zero, the phase frequency signal and the amplitude frequency envelope signal are phase locked.

In yet another case, the heights ratio is updated for each of the plurality of samples.

In yet another case, extracting the extract a phase-amplitude coupling measure comprises defining the time series in the complex plane by representing each instantaneous amplitude point in the time series by a magnitude of a complex vector and the modulating signal phase by a vector angle of the complex vector.

In yet another case, phase-amplitude coupling is represented by an approximately non-uniform circular distribution in a mapping of the time series in the complex plane.

In yet another case, the one or more processors are further configured to execute a surrogate analysis module to determine a surrogate distribution associated with a statistical significance of at least one measure of the cross-frequency coupling, determining the surrogate distribution comprising repeating at least one of the determination of MVL-MI and the determination of CF-PLV with randomized version of the amplitude signal and determining a statistical value associated with significance across a set of values from each iteration in the surrogate distribution, wherein the output module further configured to output the statistical value associated with significance.

In another aspect, there is provided a computer-implemented method for neural cross-frequency coupling analysis, comprising: receiving neural signals; extracting a phase frequency signal and an amplitude frequency envelope signal from each of the neural signals; determining a first measure of cross-frequency coupling comprising a mean vector length modulation index (MVL-MI), determining the MVL-MI comprises determining a magnitude of an averaged complex-valued time series from a plurality of samples of the neural signals to extract a phase-amplitude coupling measure, each sample associated with a respective one of the amplitude frequency envelope signals and the phase frequency signals; and outputting at least one measure of the cross-frequency coupling.

In a particular case, the method further comprising determining a second measure of cross-frequency coupling comprising a cross-frequency phase locking value (CF-PLV) between a phase of the phase frequency signal and a phase of the amplitude frequency envelope signal.

In another case, the method further comprising determining a third measure of a heights ratio between a maximum amplitude height and a minimum amplitude height of the amplitude frequency envelope.

In yet another case, extracting the amplitude frequency envelope signal comprises passing the neural signal through a Hilbert filter, creating a complex vector comprising real and imaginary components, and determining the magnitude of the complex vector.

In yet another case, determining the CF-PLV comprises: determining an angular difference as the phase of the phase frequency signal subtracted by the phase of the amplitude frequency envelope signal; determining an instantaneous complex vector from the angular difference averaged over the plurality of samples; and determining a magnitude of the instantaneous vector as a measure of phase locking value.

In yet another case, when the magnitude of the instantaneous vector is zero, the phase frequency signal and the amplitude frequency envelope signal are phase locked.

In yet another case, the heights ratio is updated for each of the plurality of samples.

In yet another case, extracting the extract a phase-amplitude coupling measure comprises defining the time series in the complex plane by representing each instantaneous amplitude point in the time series by a magnitude of a complex vector and the modulating signal phase by a vector angle of the complex vector.

In yet another case, phase-amplitude coupling is represented by an approximately non-uniform circular distribution in a mapping of the time series in the complex plane.

In yet another case, the method further comprising determining a surrogate distribution associated with a statistical significance of at least one measure of the cross-frequency coupling, determining the surrogate distribution comprising repeating at least one of the determination of MVL-MI and the determination of CF-PLV with randomized version of the amplitude signal and determining a statistical value associated with significance across a set of values from each iteration in the surrogate distribution, the method further comprising outputting the statistical value associated with significance.

In another aspect, there is provided a system architecture for neural cross-frequency coupling analysis by determining a mean vector length modulation index (MVL-MI), the system architecture receiving a phase frequency signal and an amplitude frequency envelope signal from each of one or more neural signals, the system architecture comprising: a Hilbert filter to apply a Hilbert transform to the phase frequency signal; a first coordinate rotation digital computer (CORDIC) to apply an ARCTAN transformation on the Hilbert transformed signal to determine a phase of the phase frequency signal; a second CORDIC to determine a complex vector using SIN components of the phase of the phase frequency signal and COS components of the phase of the phase frequency signal; a multiplier to scale the complex vector by a magnitude of the amplitude frequency envelope signal; and a third CORDIC to determine a magnitude of an averaged complex-valued time series of the combined SIN components and the combined COS components.

These and other aspects are contemplated and described herein. It will be appreciated that the foregoing summary sets out representative aspects of the system and method to assist skilled readers in understanding the following detailed description.

DESCRIPTION OF THE DRAWINGS

A greater understanding of the embodiments will be had with reference to the Figures, in which.

DETAILED DESCRIPTION

Figure 1:
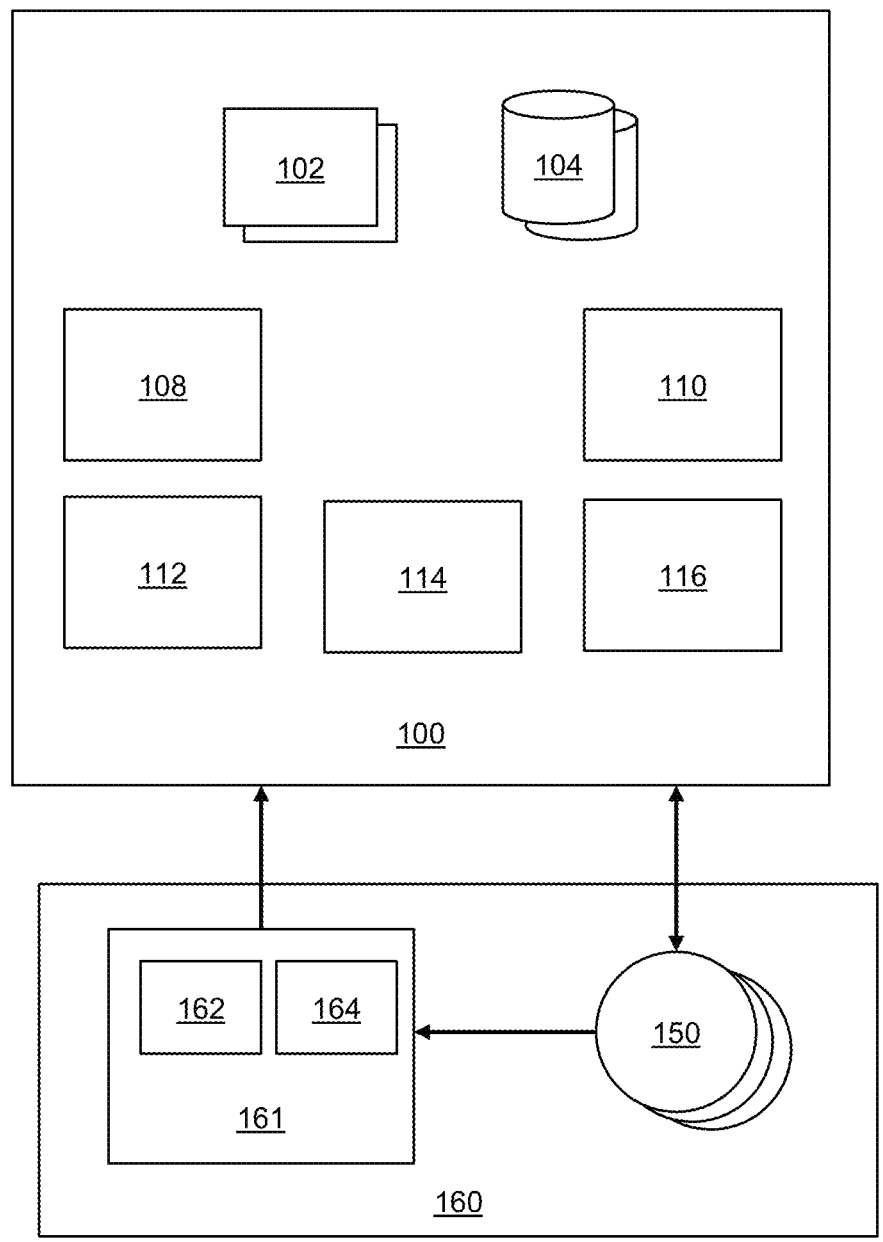
FIG. 1 shows a block diagram of an embodiment of a system for neural cross-frequency coupling analysis, according to an embodiment.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender. Further definitions for terms may be set out herein; these may apply to prior and subsequent instances of those terms, as will be understood from a reading of the present description.

Any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Embodiments described herein generally provide a system and method for neural interfacing with cross-frequency coupling.

In embodiments described herein, an architecture is provided, in some cases a VLSI architecture, which implements three selectable measures of CFC to enable the application specific compromise between low-latency and high-accuracy processing. An example of the architecture of the present embodiments has been demonstrated, using exemplary in-vitro human neocortical slice recordings, to have a latency of 48 ms.

It has been found that cross-frequency coupling (CFC) may play a functional role in biological information processing in the brain. In particular, phase-amplitude coupling (PAC) is hypothesized to provide an effective means to integrate functional systems, transferring information from large-scale brain networks operating at behavioral timescales, to rapid cortical processing.

It has been theorized that global brain rhythms modulate the excitability of local neural populations through fluctuations in membrane potentials, increasing the probability of neuronal spiking at a specific phase of slower rhythms. In electroencephalography (EEG), this mechanism can manifest itself in local field potentials that resemble amplitude modulation in electronic communication.

Abnormal CFC has been implicated in pathological brain states such as epilepsy and Parkinson's disease. CFC between pathological high frequency oscillations (pHFOs) and lower frequency rhythms are elevated in the seizure-onset zone compared to non-epileptic regions, and exaggerated PAC has been observed in the primary motor cortex of Parkinson's Disease patients. In some cases, a reduction in excessive coupling has been shown to be effective neuromodulation treatments. The present inventors recognized that CFC may be a useful feedback measure for use in closed-loop neural stimulation devices.

Depending on the application, in some cases, a compromise may have to be made between precision and computational efficiency. In applications utilizing closed-loop processing based on CFC, a low-latency may be required to quickly determine parameters for responsive neural stimulation. Such experiments performed in-vivo may require the use of implantable microsystems, which typically operate under highly power-constrained conditions. The configurable architecture of the present embodiments can support three metrics to enable the application-specific tradeoff between, for example, low-power, low-latency and high-precision.

Furthermore, a computational overhead of such an architecture can routinely involve determining the statistical significance of a given measure of CFC. The architecture of the present embodiments advantageously supports this functionality by efficiently performing surrogate statistical analysis; in some cases, at the expense of increased latency and power-consumption.

In some of the present embodiments, three measures of CFC can be used to enable an application specific tradeoff between sample latency ($T_s$) and precision. A Cross-Frequency Phase Locking Value (CF-PLV) can be used to detect cross-frequency synchrony between a low frequency phase and a high frequency envelope phase of a recorded local field potential of the neural signal (as diagrammatically illustrated in FIG. 13). The CF-PLV generally does not quantify the relative amplitude of modulation, and so a Heights Ratio (HR) can be used to compliment this measurement. A Mean Vector Length Modulation Index (MVL-MI) can be used to determine a magnitude of an averaged complex-valued time series, where each sample is comprised of an envelope amplitude of a modulated high-frequency signal and a phase of a low-frequency modulating signal. Implementation of these approaches in the context of the systems and methods of the present embodiments will be described herein. Thus, MVL-MI can be used to determine CFC. Examples of trade-offs between these three measures can be seen in FIGS. 12A and 12B; where, generally, MVL-MI uses fewer processor clock cycles than the combination of CF-PLV and HR. In some cases, any one of the above measures can be used. In further cases, a combination of measures, or all three measures, can be used. The selection of which measure to use can be made depending on a level of accuracy desired (for example, surface vs. intracranial EEG). HR generally provides the lowest accuracy of the three measures, and in most practical cases, should be used in combination with CF-PLV. Particularly, HR is essentially a measure of the "intensity" CFC and assumes that it is present; which, in some cases, may not be the case. CF-PLV generally indicates if there is CFC and HR generally indicates how much. MVL-MI detects both a presence of CFC and its magnitude; however, it requires the use of multiplication and therefore, in some practical cases, it can have a higher power consumption.

Turning to FIG. 1, a system for neural cross-frequency coupling analysis 100, according to an embodiment, is shown. The system 100 is connectable to one or more neural signal receivers 160; for example, comprising one or more electrodes 150 implantable in a patient's brain via an analog front-end 161 comprising one or more neural recording channels 162 and a digital-to-analog convertor 164. In an example, the one or more electrodes 150 can be used to receive EEG readings. The system 100 includes one or more processors 102 in communication with one or more memory units 104 and the one or more neural signal receivers 160. In some cases, the data from the one or more neural signal receivers 160 can be stored on the one or more memory units 104, or other data storage device, and used by the system 100 at a later time. As described herein, the system 100 also includes various modules executed on the one or more processors 102, including a modulation signal extractor module 108, a PLV module 110, an MVL module 112, an HR module 114, a surrogate analysis module 116, and an output module 118.

Figure 2:
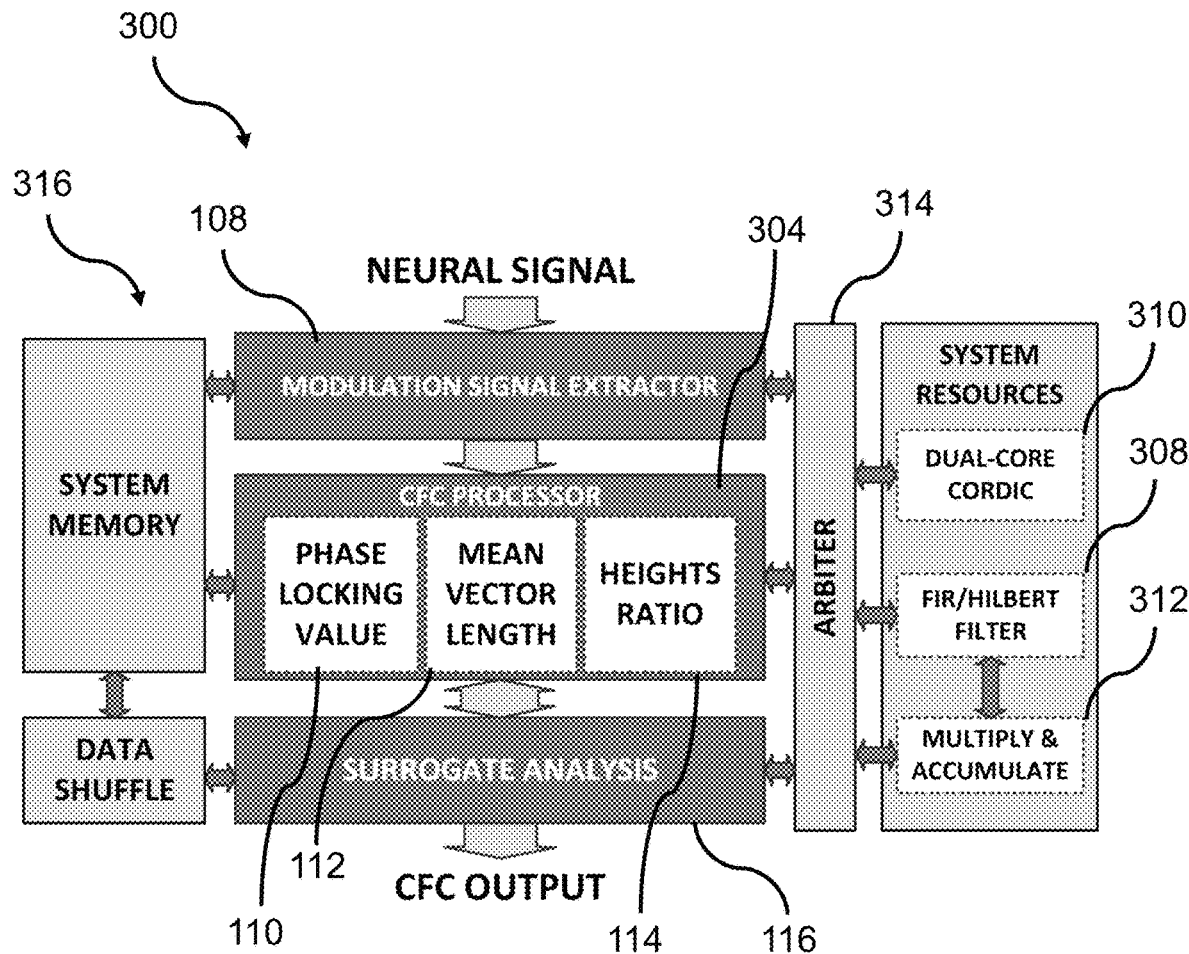
FIG. 2 diagrammatically illustrates an example architecture for the system of FIG. 1, according to an embodiment.

FIG. 2 diagrammatically illustrates an embodiment of an architecture 300 for the system 100, according to an embodiment. In an embodiment, the architecture 300 can be for an embedded system, for example, a very-large-scale integration (VLSI) integrated circuit. The system architecture 300 includes the modulation signal extractor module 108, a CFC module 304, and the surrogate analysis module 116. The CFC module 304 includes the PLV module 110, the MVL module 112, the HR module 114. In some cases, processing blocks to execute the modules can share common resources which can be time-multiplexed between processing stages via an arbiter 314. The processing blocks can include, for example, a configurable 512-tap Finite Impulse Response (FIR) filter 308 supporting both linear-phase bandpass and Hilbert transform functionality, a dual-core Coordinate Rotation Digital Computer (CORDIC) block 310 that supports both rotational and vectoring modes in a circular configuration, and a 32-bit low-power optimized multiply and accumulate block (MAC) 312. The architecture 300 can include data storage and handling modules 316; for example, system memory 104 and data shuffling modules.

Figure 3:
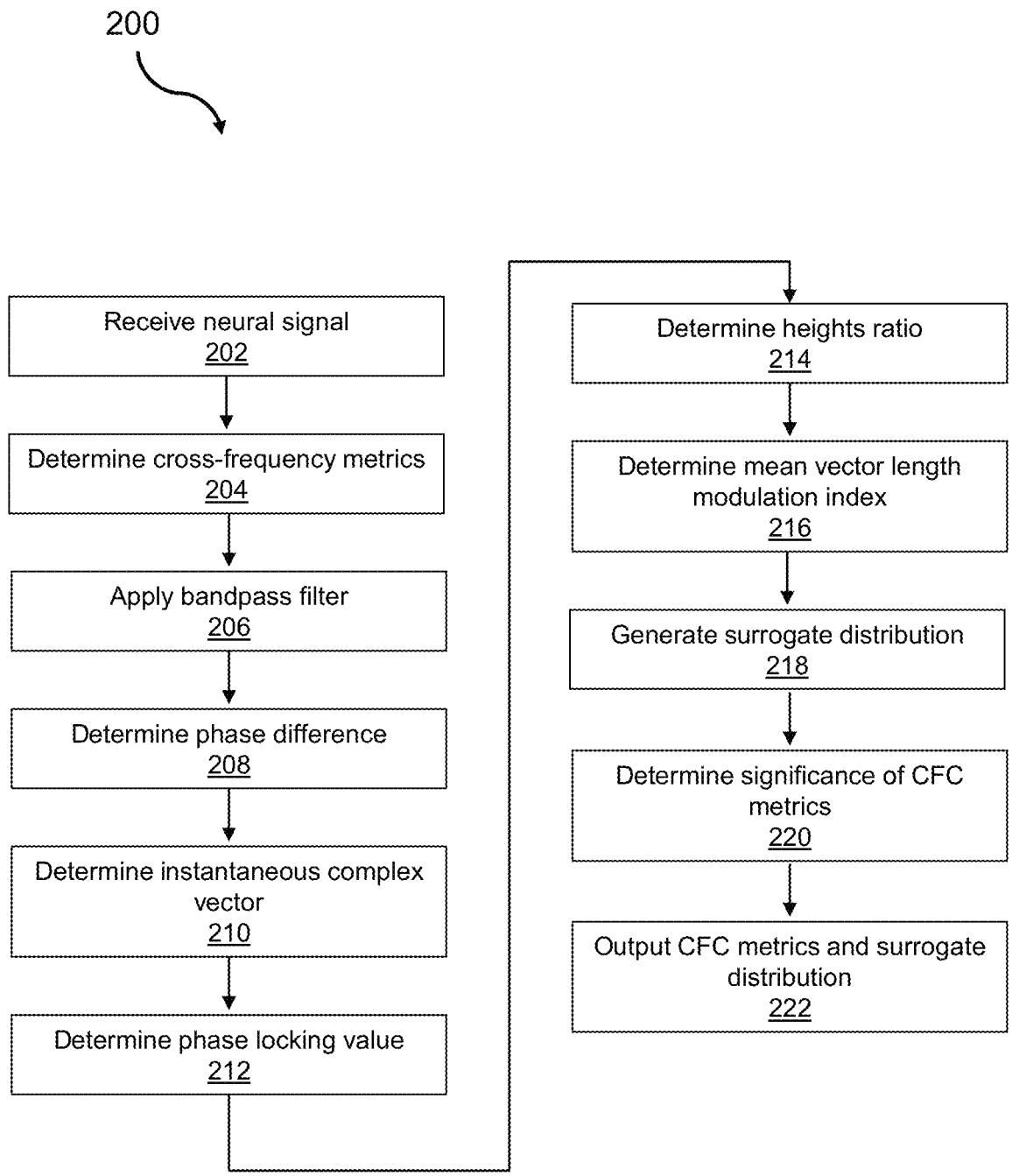
FIG. 3 shows a flowchart for a method for neural cross-frequency coupling analysis, according to an embodiment.

FIG. 3 illustrates a method for neural cross-frequency coupling analysis 200, according to an embodiment. At block 202, neural signals are received from a subject via the one or more neural signal receivers 160. In an example embodiment, the neural signals comprise electroencephalography (EEG) signals. Modulation signal extraction can then be performed by the modulation signal extractor module 108. At block 204, for modulation signal extraction, cross-frequency metrics can be determined by extracting "phase-modulating" signals and "amplitude-modulated" signals from the neural signals. These can be referred to as phase frequency ($f_p$) and amplitude frequency envelope ($f_A$), respectively. In an experimental example, theta modulated high-gamma oscillations have been observed where $f_p$ is in the range of approximately 4-8 Hz and the $f_A$ carrier is in the range of approximately 50-200 Hz.

At block 206, in some cases for modulation signal extraction, the raw EEG signal, x(t), can be bandpass filtered using a linear-phase FIR filter to extract both $f_p$(t) and a high-frequency modulated signal (for example, high-gamma modulated signal). Once the modulated high-gamma modulated signal has been isolated, its amplitude envelope time series, $f_A$(t), can be extracted (as diagrammatically illustrated in FIG. 4). In this example, an analytic signal is first formed by passing the modulated high-gamma modulated signal through a Hilbert filter, creating both real and imaginary components. The amplitude of the high-gamma envelope, $f_A$(t), can then be extracted by taking the magnitude of the complex vector of $f_A$(t). The theta modulating signal ($f_p$) can be extracted with filter delay matching as described herein.

CF-PLV determination can be performed by the PLV module 110. A primary goal of the CF-PLV determination is to detect cross-frequency synchrony between the phase of the low frequency modulating signal ($\varphi_{fp(t)}$), and the phase of the envelope extracted from the high frequency modulated signal ($\varphi_{fA(t)}$). Where $\varphi_{fp(t)}$ is an extracted phase time series of $f_p$(t), and $\varphi_{fA(t)}$ is an extracted phase time series of $f_A$(t). At block 208, a phase difference between both signals is calculated as $$\Delta\varphi_{(t)} = \varphi_{fA(t)} - \varphi_{fp(t)} \quad (1)$$

Figure 4:
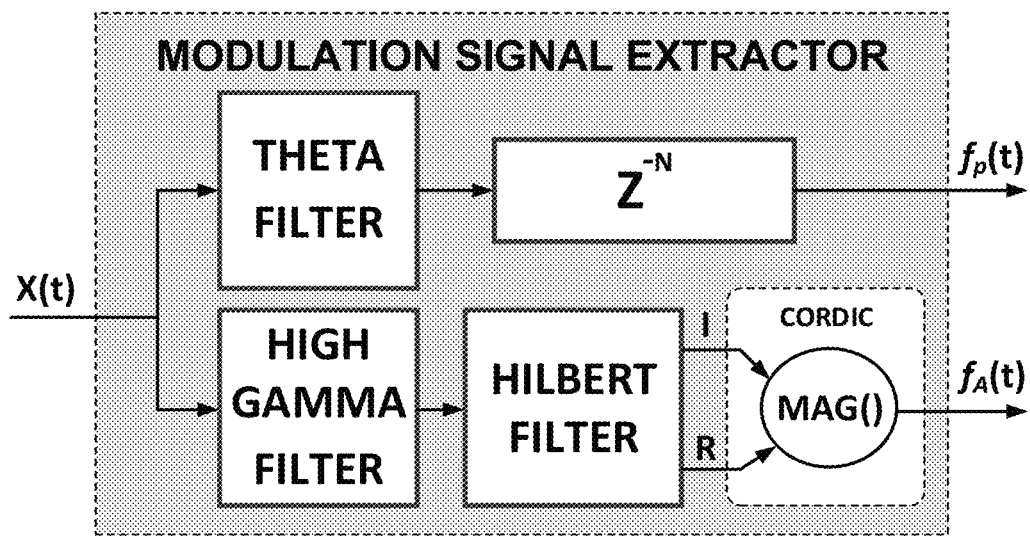
FIG. 4 diagrammatically illustrates an example architecture for a modulation signal extractor according to the system of FIG. 1.

With reference to the architecture of FIG. 4, a hypothetical example can involve having one electrode connected to a motor cortex of a human subject. It can be assumed that when the subject moves their hand, the system can determine both gamma and theta activity at that site, but probably not see any CFC. However, when the subject is experiencing a tremor, the system can determine that there is CFC between the above two bands; i.e., the phase $\varphi_{fp(t)}$ is locked to $\varphi_{fA(t)}$. The system can filter such specific frequency bands, as described, because they have been determined to be physiologically relevant.

At block 210, the above angle in calculation (1) is used to create an instantaneous complex vector that is averaged over N samples, as calculated in calculation (2). At block 212, a magnitude of this average vector is used to determine a measure of phase locking value (PLV). If the average $\Delta\varphi_i$ is 0, both $f_p$(t) and $f_A$(t) are phase-locked.

$$PLV = \frac{1}{N}\sqrt{\left(\sum_{t=0}^{N-1}(\cos(\Delta\varphi_{(t)}))\right)^2 + \left(\sum_{t=0}^{N-1}(\sin(\Delta\varphi_{(t)}))\right)^2} \quad (2)$$

Figure 5:
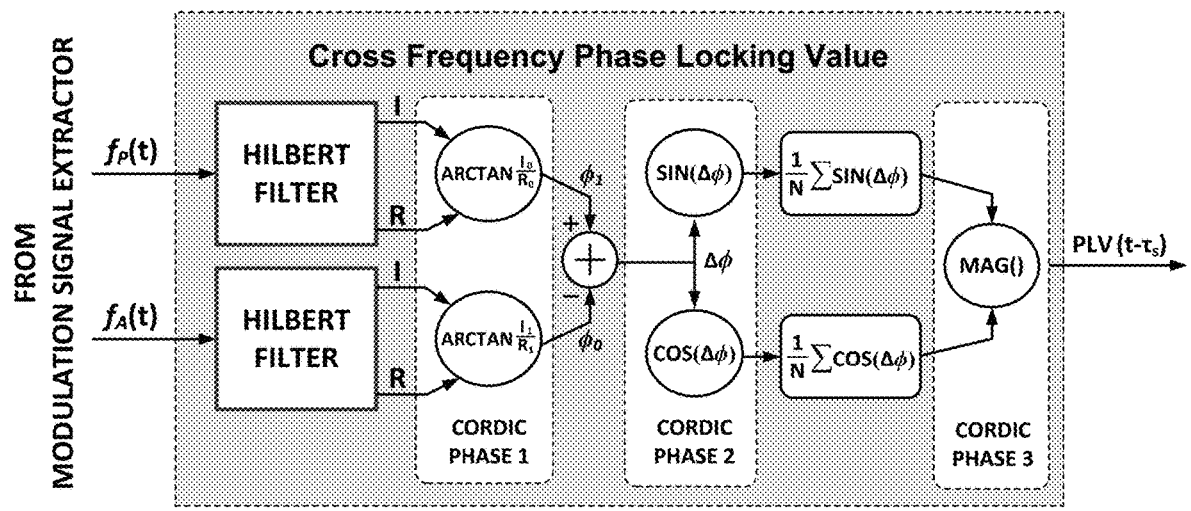
FIG. 5 diagrammatically illustrates an example architecture for determining cross frequency phase locking value.

An example VLSI architecture to determine the PLV measure is shown in FIG. 5. The envelope time series can first be filtered using the same parameters as used for $f_p$. Following this, analytic signals for both $f_p$(t) and $f_A$(t) can be created using a Hilbert transform. The PLV can be determined for the phase modulating theta signal and the extracted envelope of the amplitude modulated high-gamma signal.

The implementation of the PLV approach of the present embodiments can offers several advantages over conventional approaches. For example, FIR based moving average filters can be replaced by an IIR approximation, resulting in an approximately 60% decrease in latency. Furthermore, the number of dual-core coordinate rotation digital computer (CORDIC) cores can be reduced from five to two by adding system arbitration to support resource reuse (as shown in FIG. 5, only two CORDIC blocks need to be used at a given time). This optimization can result in a silicon area reduction of over eight-times with effectively very little impact on latency. While use of CORDIC approaches are described herein, other computing approaches may be used.

With reference to the example architecture of FIG. 5, Hilbert filtering is performed by convolving pre-calculated antisymmetric coefficients with the bandpass filtered phase frequency and amplitude frequency signals. Advantageously, this creates an analytic signal for which an instantaneous phase can be calculated using the CORDIC cores can perform ARCTAN operations. A determination of the sine and cosine of such angle is performed to form a complex vector which is integrated and averaged over time with two moving average filters. The magnitude of this average complex vector can be determined to provide the CF-PLV output.

Figures 6A, 6B:
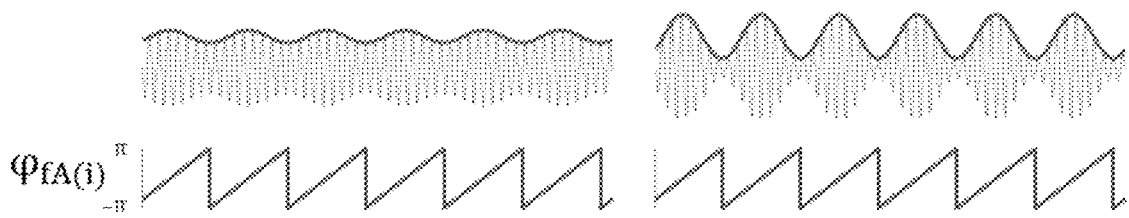
FIGS. 6A and 6B illustrate two example signals, respectively, that have approximately a same coupling measure independent of a relative amplitude of modulation.
Figure 7:
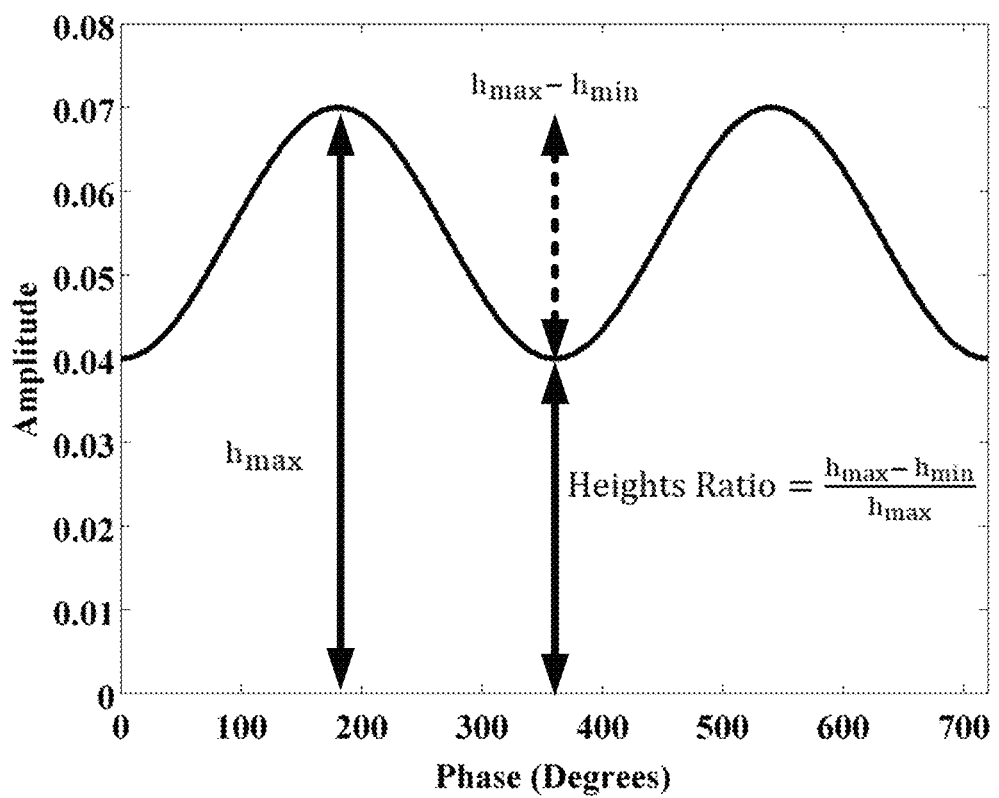
FIG. 7 illustrates an example of a heights ratio determination for a signal.

At block 214, a heights ratio can be determined by the HR module 114. In some cases, a limitation of the CF-PLV measure is, for example as highlighted in FIGS. 6A and 6B, where both signals can result in the same coupling measure independent of the relative amplitude of modulation. In this case, phase alone may not reflect the intensity of high-frequency modulation, as $\varphi_{fA}$ is the same for the examples in FIG. 6A and FIG. 6B. One approach to address this issue involves using the heights ratio determination to compliment the CF-PLV value (as illustrated in FIG. 7); where $h_{max}$ and $h_{min}$ are maximum and minimum heights, respectively, taken from the extracted $f_A$(t) envelope. Thus, the heights ratio being ($h_{max} - h_{min}$)/$h_{max}$. In some cases, when enabled, these values, and the heights ratio, can be updated for each new sample.

At block 216, a mean vector length modulation index (MVL-MI) can be determined by the MVL module 112 as a magnitude of an average value of a complex-valued time series, as calculated in calculation (3). Each sample point is comprised of the amplitude of the modulated high-frequency envelope, and the phase of the low-frequency modulating signal.

$$z(t) = A_{HF} e^{i\varphi_{LF}(t)} \quad (3)$$

Where $A_{HF}$ is an amplitude of the high frequency envelope at sample t, and $e^{i\varphi_{LF}(t)}$ is a complex vector formed using a phase of the low frequency modulating signal: $e^{i\varphi_{LF}(t)} = \cos(\varphi_{LF}(t)) + j \sin(\varphi_{LF}(t))$.

A time series defined in the complex plane can be used to extract a phase-amplitude coupling measure. Each instantaneous amplitude point can be represented by a length of a complex vector, whereas the modulating signal phase of the time point is represented by an angle of the complex vector. A magnitude of the average complex vector of this time series reflects the raw modulation index, as calculated in calculation (4). A surrogate analysis can then be performed to determine the statistical significance of the measure for a final modulation index as described herein.

$$m_{raw} = |\overline{z(t)}| \quad (4)$$

Figures 8A, 8B:
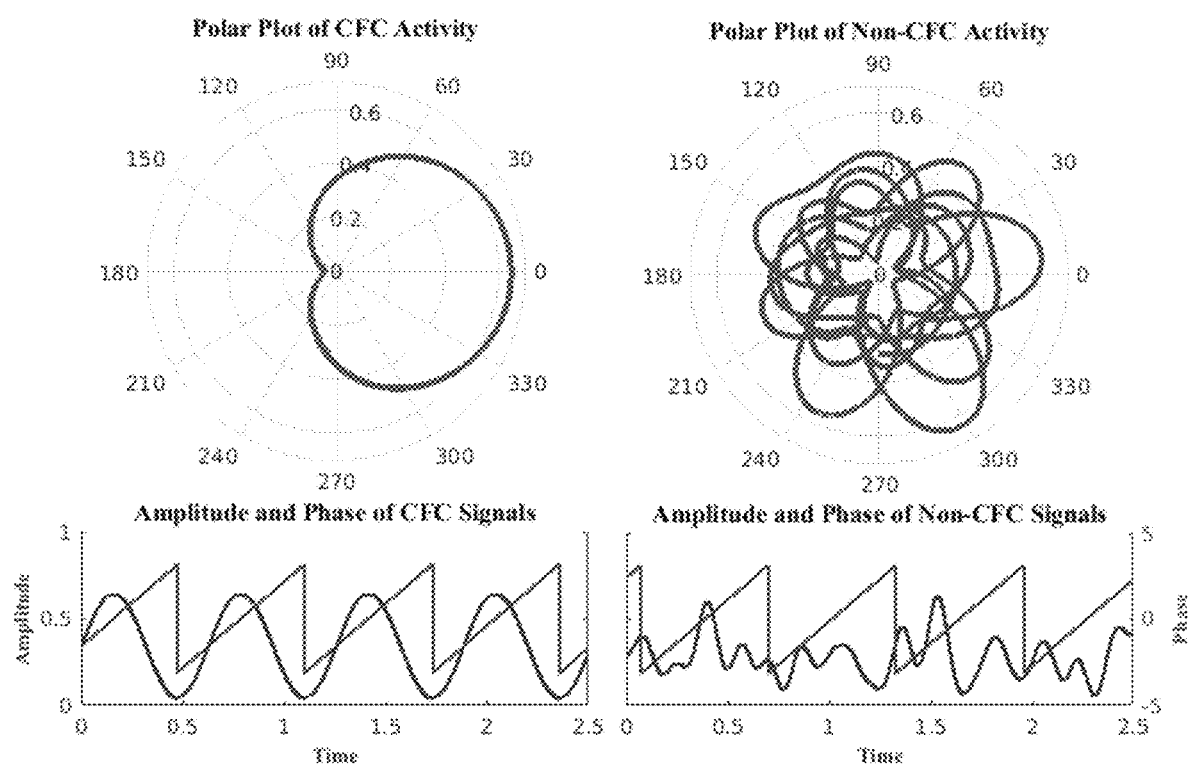
FIG. 8A illustrates an exemplary mean vector length modulation index complex vector series with a bump at 0 degrees in the complex plane.
FIG. 8B illustrates an exemplary mean vector length modulation index complex vector series with a uniform circular density.

In the case of an absence of phase-amplitude coupling, a plot of the time series in the complex plane is generally characterized by a roughly uniform circular density of vector points, symmetric around zero, as illustrated in FIGS. 8A and 8B. FIGS. 8A and 8B illustrate an exemplary MVL-MI complex vector series. A bump at 0 degrees in the complex plane generally indicates phase-amplitude coupling (PAC), as shown in FIG. 8A. A uniform circular density generally indicates no relationship between phase and amplitude, as shown in FIG. 8B. If there is modulation of the high-frequency amplitude by the $f_p(t)$ phase, the $f_A(t)$ envelope is higher at certain phases than others. This higher amplitude for certain angles will lead to a "bump" in the complex plane plot, leading to loss of symmetry around zero. This loss of symmetry can be inferred by determining the length of the average vector of all points in the complex plane. As a lack of coupling results in a symmetric distribution around zero, a resulting mean vector length is relatively small. The existence of coupling leads to a non-uniform circular distribution, resulting in a larger mean vector length. The MVL-MI can be determined, for example, using the diagrammatic mean vector length modulation index architecture shown in FIG. 9, for the phase modulating signal and extracted envelope.

Figure 9:
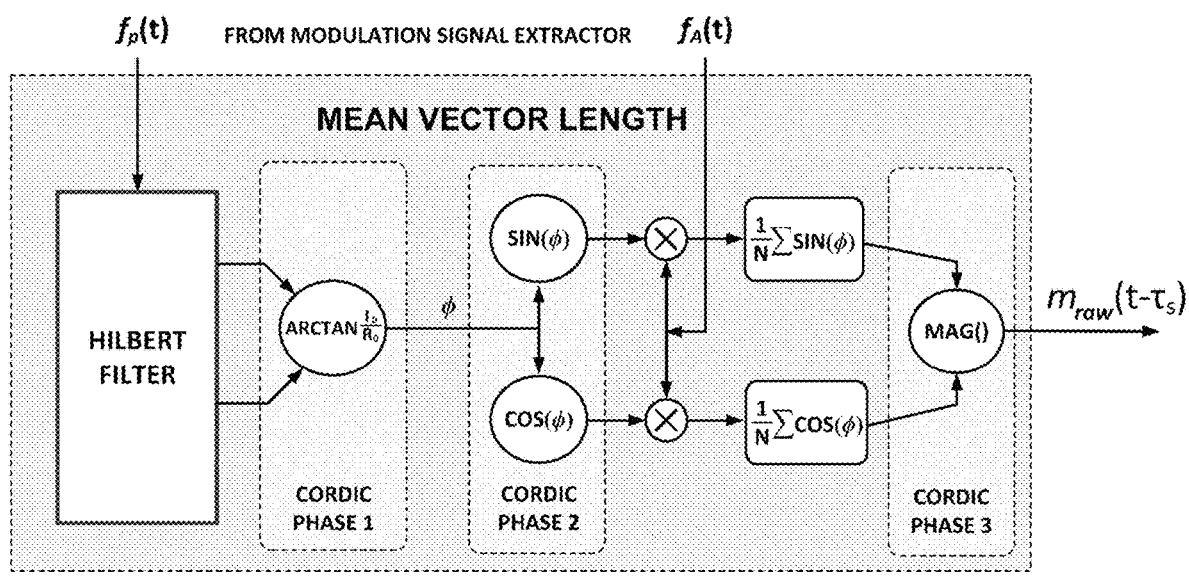
FIG. 9 diagrammatically illustrates an example architecture for determining a mean vector length, according to the system of FIG. 1.

With reference to the example architecture of FIG. 9, a Hilbert filter can be used to apply a Hilbert transform to the phase frequency signal. A first coordinate rotation digital computer (CORDIC) can be used to apply an ARCTAN transformation on the Hilbert transformed signal to determine a phase of the phase frequency signal. A second CORDIC can be used to construct a complex vector using SIN and COS components of the phase of the phase frequency signal. This complex vector can then be scaled by multiplying the complex vector by a magnitude of the amplitude frequency envelope signal. A third CORDIC can be used to determine a magnitude of an averaged complex-valued time series of the combined SIN components and the combined COS components.

Figure 14:
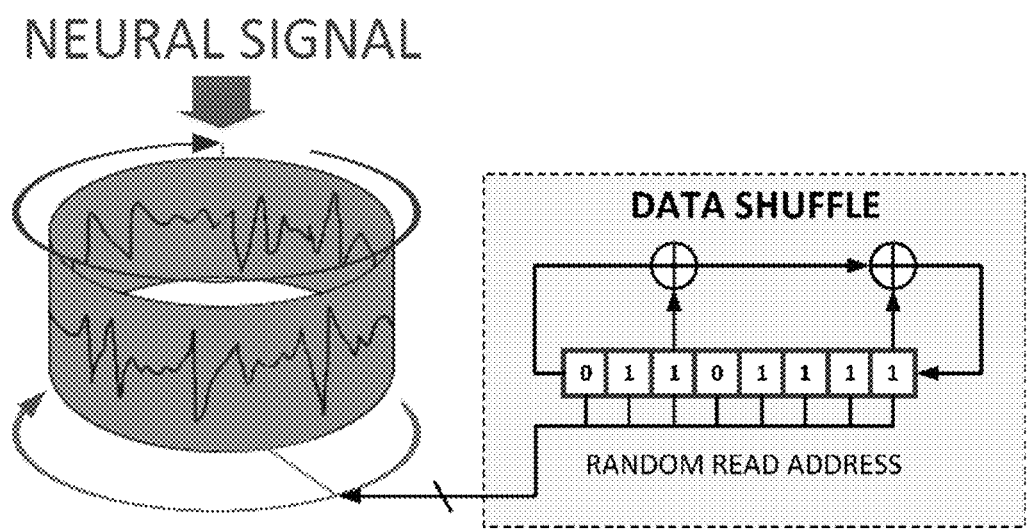
FIG. 14 illustrates an exemplary diagram of using a random access circular sample buffer to determine a surrogate distribution.

In some cases, to consider a level of statistical significance of the estimated cross-frequency coupling (CFC) metrics (phase locking value, mean vector length, and heights ratio), at block 218, a surrogate distribution can be determined by the surrogate analysis module 116, to consider a level of statistical significance of the estimated CFC metrics, by repeating the determination of either MVL-MI or CF-PLV, or both, with shuffled versions of the amplitude signal, $f_A(t)$. In some cases, this approach can be accelerated using a random access circular sample buffer that is used for inter-sample memory storage, as exemplary illustrated in FIG. 14.

As part of the surrogate distribution generation, in some cases, a random selection for a start point in each shuffle iteration is performed using a linear feedback shift register (LFSR) as a pseudorandom number generator. This acts as a memory address generator to access a random start points in the circular buffer, from which the surrogate distribution can be generated. In further cases, other approaches to finding a random memory address can be used.

At block 220, a mean, $\mu$, and/or a variance, mean absolute deviation (MAD), can be calculated by the surrogate analysis module 116 across the set of values from each iteration in the surrogate distribution; which can then be used to assess the significance of the CFC metrics. In an example, as experimentally determined by the present inventors, 50 permutations can provide a sufficient significance determination; however, the number of permutations can be increased dynamically, depending on the required accuracy.

At block 222, the CFC is outputted by the output module 118. In some cases, this can include outputting at least one of the PLV determination, MVL determination, HR determination, and surrogate distribution and analysis by the output module 118. In an example, the output of the output module 118 can be communicated as a feedback measure in a closed-loop neural stimulation device. In another example, the output of the output module 118 can be displayed or otherwise presented to a user via an output device (for example, a computer display and/or speakers).

Figure 10:
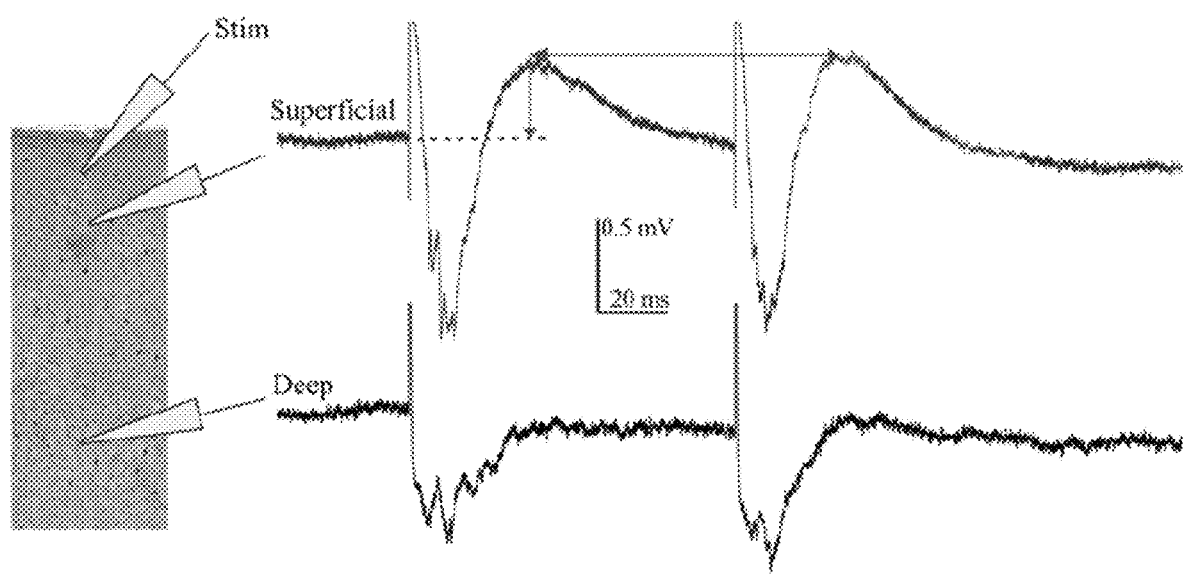
FIG. 10 diagrammatically illustrates an example slice electrode experimental arrangement.

In an experimental example performed by the present inventors, the functionality of the architecture of the present embodiments was verified using data obtained at a local hospital. Neural signals were captured by recording local field potentials (LFPs) simultaneously in superficial (layers II/III) and deep (layers V-VI) layers in 500 um thick human temporal cortical slices using a single glass electrode in each layer filled with a solution containing 150 mM NaCl or a standard artificial cerebrospinal fluid (ACSF). This slice electrode experimental arrangement is diagrammatically illustrated in FIG. 10.

Figure 11:
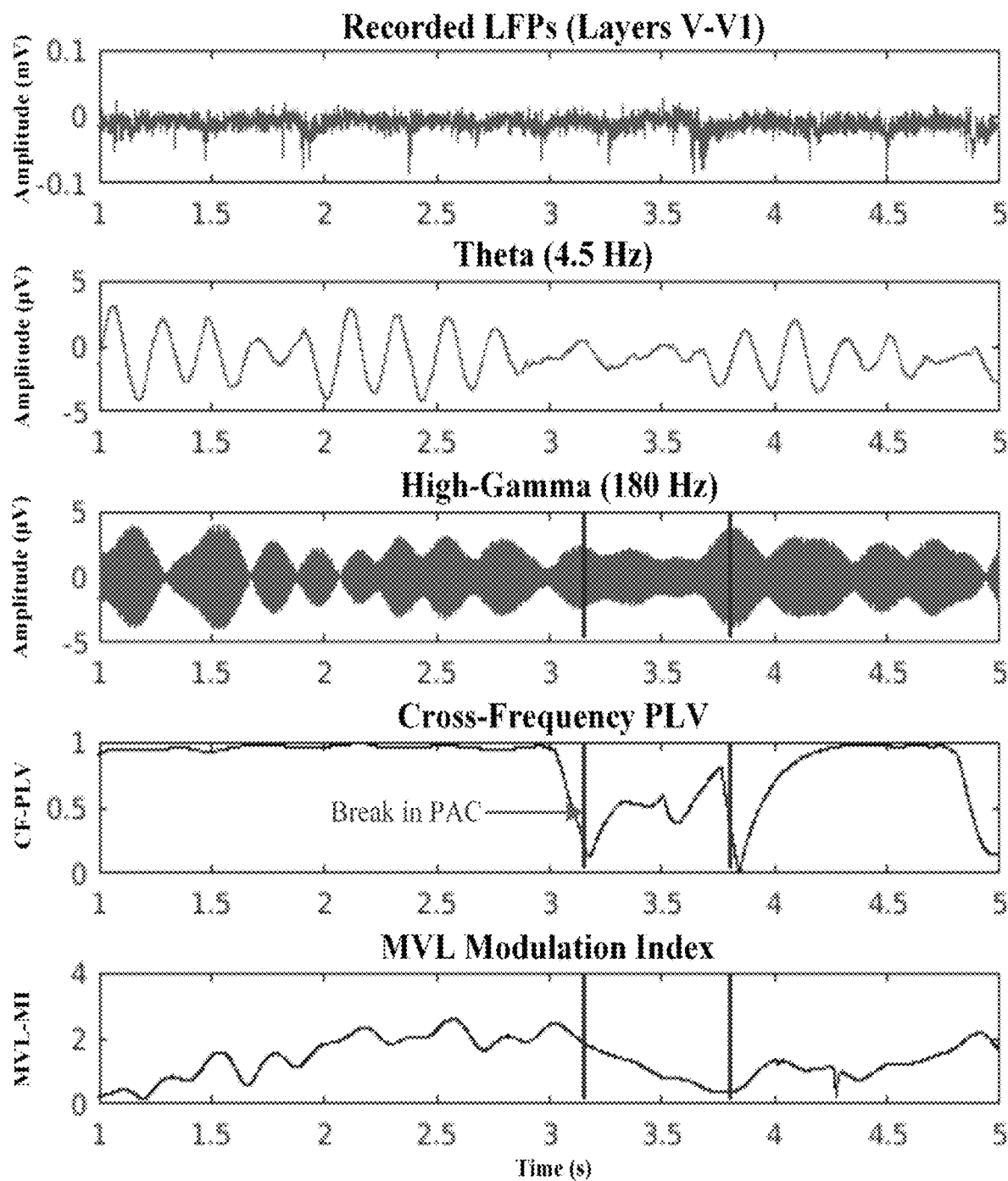
FIG. 11 illustrates example experimental measurements for neural signals, phase locking value, and mean vector length, using the system of FIG. 1.

For each slice, a single 30 second region displaying the largest power increase during kainate plus carbachol conditions was analyzed. Computed measures of PAC using MVL-MI and CF-PLV from this example experiment are illustrated in FIG. 11. A sub segment of phase-amplitude coupling (PAC) was used to demonstrate the functionality of the architecture and was down-sampled to a 1 kHz sample rate. The accuracy of each metric was evaluated using 16-bit fixed point implementation. Generally, both CF-PLV and the MVL-MI are sensitive to the intensity of PAC. CF-PLV had a range of 0 to 1 and MVL-MI was unconstrained.

Figure 12A:
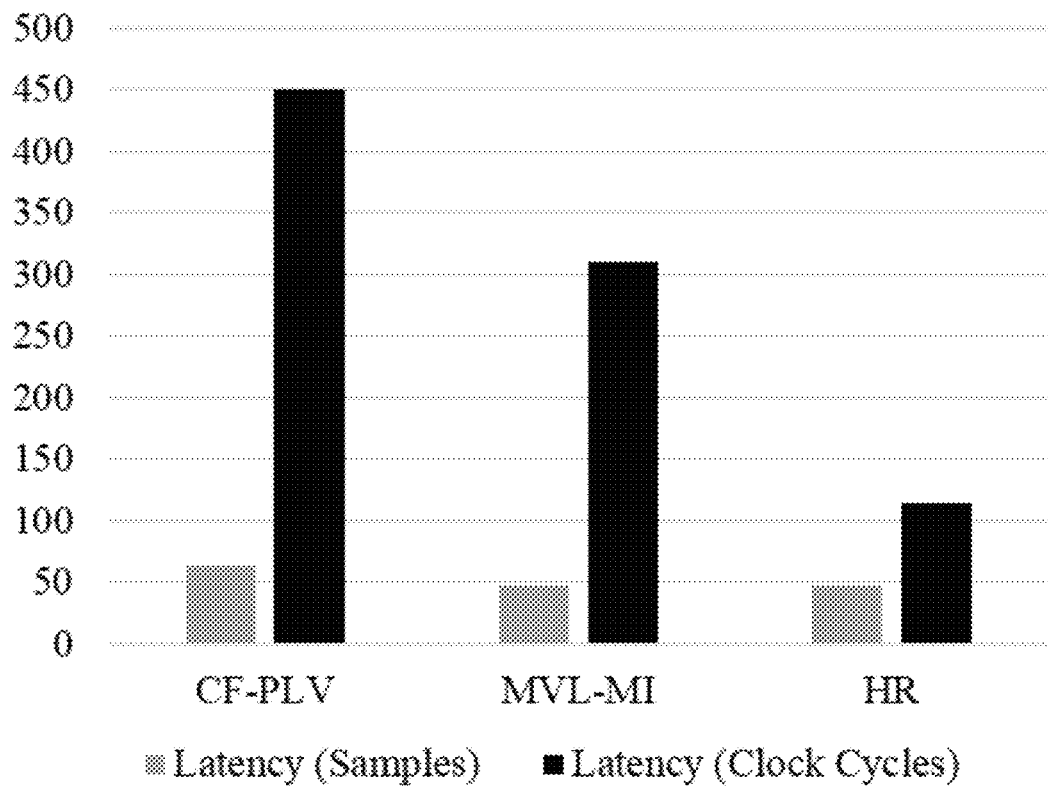
FIG. 12A illustrates a comparison of experimental processing and sample latency.
Figure 12B:
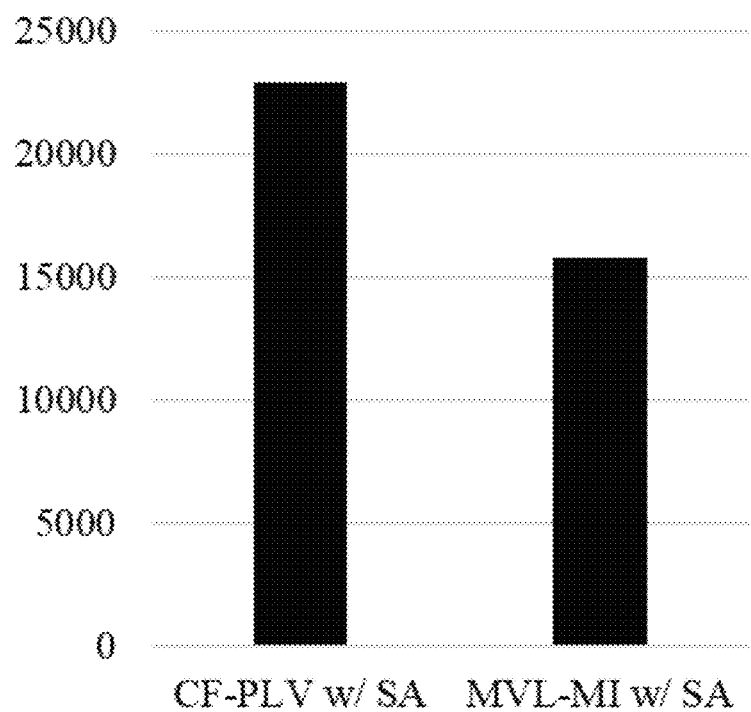
FIG. 12B illustrates experimentally determined overhead to perform surrogate analysis for phase locking value and mean vector length.
Figure 13:
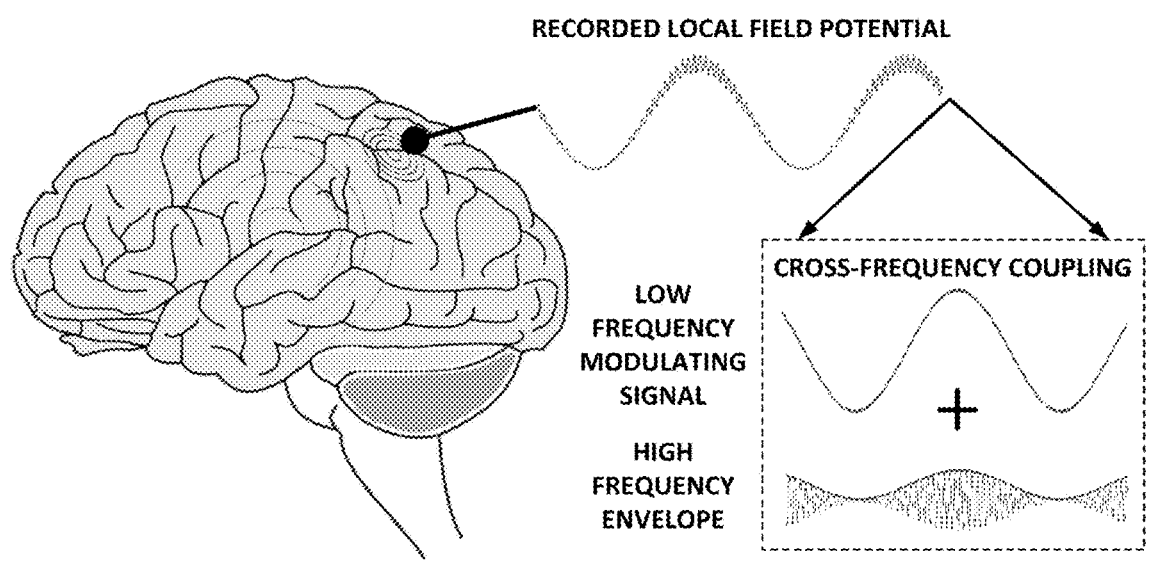
FIG. 13 diagrammatically illustrates cross-frequency coupling being used to detect a low frequency modulating signal and a high frequency envelope phase of a recorded local field potential of a neural signal.

Output latency for each reported metric is shown in FIGS. 12A and 12B with processing clock cycles on the vertical axis. FIG. 12A illustrates processing and sample latency comparison. FIG. 12B illustrates overhead to perform surrogate analysis (n=50) for a metric. In this case, heights ratio (HR) offers the lowest processing latency with a sample latency equivalent to that of MVL-MI. While the introduction of surrogate analysis does not impact the sample latency, the processing latency increases almost linearly with each iteration as the metric is computed for each surrogate. A greater number of CPU cycles directly increases the power required for a given CFC metric.

The embodiments described herein provide an architecture to detect cross-frequency coupling in neural signals, and an example of which has been experimentally validated using in-vitro human slice recordings. Advantageously, the embodiments described herein provide processing latency that is minimized to enable highly-responsive interaction with neural systems under investigation. For better time resolution and precision, CF-PLV can be used. However, this measurement generally comes at the expense of increased latency. The MVL-MI approach of the present embodiments advantageously offers a beneficial compromise between power and latency. The HR approach generally comes at the lowest relative computational expense. Advantageously, the present embodiments allow for the implementation of these measures with a power efficiency suitable for implantable devices, enabling responsive closed-loop in-vivo experiments involving CFC.

Although the foregoing has been described with reference to certain specific embodiments, various modifications thereto will be apparent to those skilled in the art without departing from the spirit and scope of the invention as outlined in the appended claims. The entire disclosures of all references recited above are incorporated herein by reference.

The invention claimed is:

1. A system for neural cross-frequency coupling analysis, the system connectable to one or more neural signal receivers to receive neural signals, the system comprising one or more processors and one or more memory units, the one or more processors in communication with the one or more memory units and configured to execute:
a modulation signal extractor module to extract a phase frequency signal and an amplitude frequency envelope signal from each of the neural signals;
a mean vector length (MVL) module to determine a first measure of cross-frequency coupling, the first measure of cross-frequency coupling comprising a mean vector length modulation index (MVL-MI), determining the MVL-MI comprises determining a magnitude of an averaged complex-valued time series from a plurality of samples of the neural signals, each sample associated with a respective one of the amplitude frequency envelope signals and the phase frequency signals, the MVL module extracting a phase-amplitude coupling measure using the magnitude of the averaged complex-valued time series; and
an output module to output at least one measure of the cross-frequency coupling to indicate a pathological brain state, the at least one measure comprising the phase-amplitude coupling measure.

2. The system of claim 1, wherein the one or more processors are further configured to execute a phase locking value (PLV) module to determine a second measure of cross-frequency coupling, the second measure of cross-frequency coupling comprising a cross-frequency phase locking value (CF-PLV) between a phase of the phase frequency signal and a phase of the amplitude frequency envelope signal.

3. The system of claim 2, wherein the one or more processors are further configured to execute a heights ratio (HR) module to determine a third measure of a heights ratio between a maximum amplitude height and a minimum amplitude height of the amplitude frequency envelope.

4. The system of claim 1, wherein the modulation signal extractor module extracts the amplitude frequency envelope signal by passing the neural signal through a Hilbert filter, creating a complex vector comprising real and imaginary components, and determining the magnitude of the complex vector.

5. The system of claim 2, wherein determining the CF-PLV comprises:
determining an angular difference as the phase of the phase frequency signal subtracted by the phase of the amplitude frequency envelope signal;
determining an instantaneous complex vector from the angular difference averaged over the plurality of samples; and
determining a magnitude of the instantaneous vector as a measure of phase locking value.

6. The system of claim 5, wherein when the magnitude of the instantaneous vector is zero, the phase frequency signal and the amplitude frequency envelope signal are phase locked.

7. The system of claim 3, wherein the heights ratio is updated for each of the plurality of samples.

8. The system of claim 1, wherein extracting the phase-amplitude coupling measure comprises defining the time series in the complex plane by representing each instantaneous amplitude point in the time series by a magnitude of a complex vector and the modulating signal phase by a vector angle of the complex vector.

9. The system of claim 8, wherein phase-amplitude coupling is represented by an approximately non-uniform circular distribution in a mapping of the time series in the complex plane.

10. The system of claim 3, wherein the one or more processors are further configured to execute a surrogate analysis module to determine a surrogate distribution associated with a statistical significance of at least one measure of the cross-frequency coupling, determining the surrogate distribution comprising repeating at least one of the determination of MVL-MI and the determination of CF-PLV with randomized version of the amplitude signal and determining a statistical value associated with significance across a set of values from each iteration in the surrogate distribution, wherein the output module further configured to output the statistical value associated with significance.

11. A computer-implemented method for neural cross-frequency coupling analysis, comprising:
receiving neural signals;
extracting a phase frequency signal and an amplitude frequency envelope signal from each of the neural signals;
determining a first measure of cross-frequency coupling, the first measure of cross-frequency coupling comprising a mean vector length modulation index (MVL-MI), determining the MVL-MI comprises determining a magnitude of an averaged complex-valued time series from a plurality of samples of the neural signals, each sample associated with a respective one of the amplitude frequency envelope signals and the phase frequency signals, extracting a phase-amplitude coupling measure using the magnitude of the averaged complex-valued time series; and
outputting at least one measure of the cross-frequency coupling to indicate a pathological brain state, the at least one measure comprising the phase-amplitude coupling measure.

12. The method of claim 11, further comprising determining a second measure of cross-frequency coupling, the second measure of cross-frequency coupling comprising a cross-frequency phase locking value (CF-PLV) between a phase of the phase frequency signal and a phase of the amplitude frequency envelope signal.

13. The method of claim 12, further comprising determining a third measure of a heights ratio between a maximum amplitude height and a minimum amplitude height of the amplitude frequency envelope.

14. The method of claim 11, wherein extracting the amplitude frequency envelope signal comprises passing the neural signal through a Hilbert filter, creating a complex vector comprising real and imaginary components, and determining the magnitude of the complex vector.

15. The method of claim 12, wherein determining the CF-PLV comprises:
   determining an angular difference as the phase of the phase frequency signal subtracted by the phase of the amplitude frequency envelope signal;
   determining an instantaneous complex vector from the angular difference averaged over the plurality of samples; and
   determining a magnitude of the instantaneous vector as a measure of phase locking value.

16. The method of claim 15, wherein when the magnitude of the instantaneous vector is zero, the phase frequency signal and the amplitude frequency envelope signal are phase locked.

17. The method of claim 11, wherein extracting the phase-amplitude coupling measure comprises defining the time series in the complex plane by representing each instantaneous amplitude point in the time series by a magnitude of a complex vector and the modulating signal phase by a vector angle of the complex vector.

18. The method of claim 17, wherein phase-amplitude coupling is represented by an approximately non-uniform circular distribution in a mapping of the time series in the complex plane.

19. The method of claim 13, further comprising determining a surrogate distribution associated with a statistical significance of at least one measure of the cross-frequency coupling, determining the surrogate distribution comprising repeating at least one of the determination of MVL-MI and the determination of CF-PLV with randomized version of the amplitude signal and determining a statistical value associated with significance across a set of values from each iteration in the surrogate distribution, the method further comprising outputting the statistical value associated with significance.

* * * * *